United States Patent [19]
Antich et al.

[11] Patent Number: 5,422,094
[45] Date of Patent: * Jun. 6, 1995

[54] $^{19}$F LABELLED ANTIBODIES AND FRAGMENTS THEREOF AS NMR IMAGING AND SPECTROSCOPY AGENTS

[75] Inventors: Peter P. Antich, Richardson; Padmakar Kulkarni, Dallas, both of Tex.

[73] Assignee: Board of Regents, The University of Texas System, Austin, Tex.

[*] Notice: The portion of the term of this patent subsequent to Aug. 17, 2010 has been disclaimed.

[21] Appl. No.: 107,287

[22] Filed: Aug. 16, 1993

Related U.S. Application Data

[63] Continuation-in-part of Ser. No. 482,879, Feb. 21, 1990, Pat. No. 5,236,694.

[51] Int. Cl.$^6$ .............................................. A61B 5/055
[52] U.S. Cl. .................................. 424/9.34; 436/173; 436/806; 514/12; 514/59; 530/387.1; 424/9.341
[58] Field of Search ................... 424/9; 436/173, 806; 128/653.4, 654; 514/12, 59; 530/387.1

[56] References Cited

U.S. PATENT DOCUMENTS

| | | | |
|---|---|---|---|
| 4,558,279 | 12/1985 | Ackerman et al. | 324/315 |
| 4,586,511 | 5/1986 | Clark, Jr. | 128/653 |
| 4,612,185 | 9/1986 | Dean | 424/2 |
| 4,631,190 | 12/1986 | Shen et al. | 424/85 |
| 4,639,364 | 1/1987 | Hoey | 424/9 |
| 4,640,833 | 2/1987 | Tamborski et al. | 424/5 |

(List continued on next page.)

FOREIGN PATENT DOCUMENTS 0186947 10/1985 European Pat. Off. .
WO89/02931 4/1989 WIPO .

OTHER PUBLICATIONS

Levy et al, "Synthesis and Characterization of $^{19}$F NMR Chelators for Measurement of Cytosolic Free Ca," American Journal of Physiology, 252(4):C441-C449 (1987).

Mason et al., "A Novel Editing Technique for $^{19}$F MRI: Molecule-Specific Imaging", Magnetic Resonance Imaging, 8:729-736, (19990).

Jeffrey et al., "Rapid Non-invasive Assessment of Myocardial pO2 Using $^{19}$F NMR Spectroscopy of Sequestered Perfluorocarbon Emulsion", Abstracts of the 63rd Scientific Sessions, III-685, No. 2722; Circulation, 1990, vol. 82, No. 4.

Parhami et al., "Flourine-19 Relaxation Study of Perfluoro Chemicals as Oxygen Carriers," J. Phys. Chem. 87:1928-1938 (1983).

Mason et al., Abstract; "A Non-Invasive Assessment of Myocardial Oxygen Tension," Society of Magnetic Resonance in Medicine, Ninth Annual Meeting (Aug. 18-24, 1990).

Mason et al., "Tissue Oxygenation: A Novel Determination Using $^{19}$F Surface Coil NMR Spectroscopy of Sequestered Perfluorocarbon Emulsion," Magnetic Resonance in Medicine, 18:71-79 (1991).

Berkowitz, "Quantitative Determination of the Partial Oxygen Pressure in the Vitrectomized Rabbit Eye in Vivo Using $^{19}$F NMR," Magnetic Resonance Medicine, 21:233-241 (1991).

Mason et al., Abstract, "Simultaneous Oxygen Tension and Temperature Measurements: A Novel Non-Invasive Technique", 9th International Congress of Radiation Research (1991).

Mason et al., "A Noninvasive Assessment of Myocardial Oxygen Tension: $^{19}$F NMR Spectroscopy of Se- (List continued on next page.)

Primary Examiner—Gary E. Hollinden
Attorney, Agent, or Firm—Arnold, White & Durkee

[57] ABSTRACT $^{19}$F labelled antibodies are disclosed which are useful in methods of NMR imaging and spectroscopy. The compositions comprise a $^{19}$F-containing sensor moiety and an antibody, preferably a monoclonal antibody, and can optionally also comprise a spacer moiety to separate the sensor moiety and the antibody.

15 Claims, No Drawings

U.S. PATENT DOCUMENTS

| | | | |
|---|---|---|---|
| 4,741,900 | 5/1988 | Alvarez et al. | 424/85 |
| 4,838,274 | 6/1989 | Schweighardt et al. | 128/654 |
| 5,068,098 | 11/1991 | Schweighardt et al. | 424/9 |
| 5,080,885 | 1/1992 | Long, Jr. | 424/5 |
| 5,116,599 | 5/1992 | Rogers, Jr. et al. | 424/9 |

(List continued on next page.)

OTHER PUBLICATIONS quested Perfluorocarbon Emulsion," Magnetic Resonance in Medicine, 27:310–317 (1992).

Wilson et al., "Oxygen Kinetics in Preretinal Perfluorotributylamine," Exp. Eye Res., 5:119–126 (1992).

Berkowitz et al., "Perfluorocarbon Temperature Measurements Using $^{19}$F NMR," NMR in Biomedicine, 5:65–68 (1992).

Mason et al., "Oxygen TM: A Novel Probe of Tissue Oxygen Tension," Biomta.,. Art. Cells & Immob Biotech., 20(2–4), pp. 929–932 (1992).

Shukla et al., "The Relationship of Oxygen Tension and Myocardial Mechanical Function: a $^{19}$F NMR Study," Abstracts from the 65th Scientific Sessions, American Heart Association, I-693, No. 2757; Oct. 1992, vol. 86, No. 4.

Mason et al., "A Novel Approach to Localized Oxygen Measurements in Tumours: $^{19}$F NMR of Sequestered Perfluorocarbon," 17th LH Gray Conference, Canterbury, England, Apr. 1992.

Riess, "Overview of Progress in the Fluorocarbon Approach to in vivo Oxygen Delivery," Biomat., Art. Cells & Immob. Biotech., 20(2–4), pp. 183–202 (1992).

Mason et al, "In Vivo Oxygen Tension and Temperature: Simultaneous Determination Using $^{19}$F NMR Spectroscopy of Perfluorocarbon," Magnetic Resonance in Medicine, 29:296–302 (1993).

Mason et al, "Tumor Oxygen Tension Gradients: New Evidence From $^{19}$F MRI of Perfluorocarbons," Abstract of Papers for the 41st Annual Meeting of Radiation Research Society and the 13th Annual Meeting of the North American Hyperthermia Society, Dallas, Tex., (Mar. 20–25, 1993).

Shukla et al, "Tumor Oxygen Tension: A Comparison of Perfluorocarbon $^{19}$F NMR Probes," Abstract of Papers for the 41st Annual Meeting of the Radiation Research Society and the 13th Annual Meeting of the North American Hyperthermia Society, Dallas, Tex., (Mar. 20–25, 1993).

Mason et al, "Tumor Oxygen Tension: Measurement Using Oxygen TM as a $^{19}$F NMR Probe at 4.7 T," Program and Abstracts for the 5th International Symposium on Blood Substitutes, San Diego, Calif. (Mar. 17–20, 1993).

Hees et al, "Assessment of Changes in Murine Tumor Oxygenation in Response to Nicotinamide Using $^{19}$F NMR Relaxometry of a Perfluorocarbon Emulsion," Magnetic Resonance in Medicine, 29:303–310 (1993).

"Flusol-DA 20%," Investigator's Brochure (Jun. 6, 1986).

Alliance Pharmaceutical Corp., "Publication Information" (Sep. 30, 1992).

Taylor et al, "$^{19}$F-Nuclear Magnetic Resonance: Measurements of [$O_2$] and pH in Biological Systems," Biophys. Journal, 53:227–233 (Feb., 1988).

Fishman et al, "Oxygen–Sensitive $^{19}$F NMR Imaging of the Vascular System In Vivo," Magnetic Resonance Imaging, 5:279–285 (1987).

Babcock et al, "Effect of Homonuclear J Modulation on $^{19}$F Spin–Echo Images," Magnetic Resonance in Medicine 17:179–188 (1991).

Mason et al, "A Novel Editing Technique for $^{19}$F MRI: Molecule–Specific Imaging," Magnetic Resonance Imaging 8:729–736 (1990).

Mason et al, "Perfluorocarbon Imaging In Vivo: A $^{19}$F MRI Study in Tumor–Bearing Mice," Magnetic Resonance Imaging 7:475–485 (1989).

Mason et al, "Fluorinated Polymeric Molecular Probes for Non–Invasive Assessment of pH by Magnetic Resonance Spectroscopy," Abstract form, The Society of Nuclear Medicine 39th Annual Meeting, Los Angeles, Calif. (Jun. 9–12, 1992).

Mehta et al, "Novel Fluorinated Polymeric Molecular Probes for F-19 Magnetic Resonance Imaging: Syntheses & Characterization of Fluorinated Biopolymers," Abstract Pap. Am. Chem. Soc., 202:102 (1991).

Mason et al, "In Vivo Oxygen Tension and Temperature: Stimulaneous Determination Using $^{19}$F NMR Spectroscopy of Perfluorocarbon," 1991, Society of Magnetic Resonance in Medicine.

Mehta et al, "New $^{19}$F Magnetic Resonance Imaging (List continued on next page.)

U.S. PATENT DOCUMENTS

| | | | |
|---|---|---|---|
| 5,130,119 | 7/1992 | Blaszkiewicz et al. | 424/9 |
| 5,141,739 | 8/1992 | Jung et al. | 424/4 |
| 5,196,348 | 3/1993 | Schweighardt et al. | 436/173 |
| 5,208,324 | 5/1993 | Klaveness et al. | 534/16 |
| 5,236,694 | 8/1993 | Antich et al. | 424/9 |

OTHER PUBLICATIONS

Agents for Drug Targeting," Proceedings of the 38th Annual Meeting 32:5, No. 731 (May 1991).

Derwent Abstract No. 73-33347u (Meito Sangyo Company, Ltd.). (1973).

Miura et al, "8-Fluoro-8-Demethylriboflavin as a $^{19}$F-Probe for Flavin-Protein Interaction. A $^{19}$F NMR Study with Egg Whit Riboflavin Binding Protein," Biochemical and Biophysical Research Communications, 110:2, pp. 406-411 (Jan. 27, 1983).

Ratner et al, "$^{19}$F Magnetic Resonance Imaging of the Reticuloendothelial System," Magnetic Resonance in Medicine, 5:548-554 (1987).

Ratner et al, "Detection of Tumors with $^{19}$F Magnetic Resonance Imaging," Invest. Radiol., 23:361-364 (1988).

Taylor et al, "Fluorinated α-Methylamino Acids as $^{19}$F NMR Indicators of Intracellular pH," Biophys. Journal, 43:261-267 (Sep. 1983).

Deutsch et al, "Intracellular pH as Measured by $^{19}$F NMR$^a$," Annals New York Academy of Sciences, 508:33-47 (1987).

Metcalfe et al, "Free cytosolic $Ca^{2+}$ Measurements with Fluorine Labelled Indicators Using $^{19}$FNMR," Cell Calcium, 6:183-195 (1985).

Smith et al, "Design of an Indicator of Intracellular Free $Na^+$ Concentration Using $^{19}$F-NMR," Biochimica et Biophysica Acta, 889:72-73 (1986).

Evers et al, "The Potency of Fluorinated Ether Anesthetics Correlates With Their $^{19}$F Spin-Spin Relaxation Time in Brain Tissue," Biochemical and Biophysical Research Communications, 151:3, pp. 1039-1045 (Mar. 30, 1988).

Hull et al, "Chain-Fluorinated Polyamines as Tumour Markers," NMR in Biomedicine, 1:1, pp. 11-19 (1988).

Shimizu et al, "Tumor Imaging with Anti-CEA Antibody Labeled $^{19}$F Emulsion," Magnetic Resonance in Medicine, 5:290-295 (1987).

Shimizu et al, "Tumor Imaging with Anti-CEA Antibody Labeled $^{19}$F Emulsion," Magnetic Resonance in Medicine, 5:290-295 (1987).

Levy et al, "The Trifluoroacetylation of Insulin," Biochimica et Biophysica Acta, 310:398-405 (1973).

Wolfrom et al, "Trifluoroacetyl as an N-Protective Group in the Synthesis of Purine Nucleosides of 2-Amino-2-Deoxy-Saccharides," Carbohyd. Res., 11:63-76 (1969).

Goldberger et al, "The Reversible Masking of Amino Groups in Ribonuclease and Its Possible Usefulness in the Synthesis of the Protein," Biochemistry, 1:3, pp. 401-405 (May, 1962).

Brauer et al, "$^{19}$F Nuclear Magnetic Resonance Studies of Selectively Fluorinated Derivatives of G- and F-Actin," Biochemistry, 25:2187-2191 (1986).

Capon et al, "Fluorine-19 Magnetic Resonance Spectroscopic Investigation of the Binding of 2-deoxy-2-trifluoroacetamido-.alpha.-D-glucose to Lysozyme," Chemical Abstracts, 75(11):77211a (1971).

Hall et al, "NMR Study of the Effects of Fluorine Substituents on the Association Between Lysozyme and Derivatives of 2-amino-2-deoxy-D-Glucose," Chemical Abstracts, 78(7):39873x (1972).

Moussebois et al, "Separation of N-.alpha.-trifluoroacetyl-DL-lysine from Potassium Trifluoroacetate by Liquid Chromatograph," Chemical Abstracts, 77(15):102168x (1972).

Kricheldorf et al, "Preparation of N-trifluoroacetylamino Acids and Their Trimethylsilyl Esters," Chemical Abstracts, 81(15):91911j. (1974).

Douy et al, "Amphipathic Block Cooplymers with Two Polypeptide Blocks: Synthesis and Structural Study of Poly(n.epsilon.-trifluoroacetyl-L-Lysine)-Polysarcosine Copolymers," Chemical Abstracts, 107(5):40320p (1987).

Kol'tsova et al, "Dextran Derivatives. IV. Dextran Acylation by Imidozolides of N-protonated Amino Acids," Chemical Abstracts, 78(1):4443e (1972).

Schallenberg et al, "Ethyl Thioltrifluoroacetate as an Acetylating Agent with Particular Reference to Peptide Synthesis," Journal of American Chemical Society, 777:2779-2783 (1955).

"Modified Antibody for NMR Diagnostic Method—Comprises Reactive Antibody Modified with Fluorine cpd," Derwent Abstract, No. 88-195824 (Asahi Kasei Kogyo, 7 Jun. 1988).

$^{19}$F LABELLED ANTIBODIES AND FRAGMENTS THEREOF AS NMR IMAGING AND SPECTROSCOPY AGENTS

This is a continuation-in-part of U.S. application Ser. No. 07/482,879, filed on Feb. 21, 1990, now U.S. Pat. No. 5,236,694. That application is incorporated here by reference.

BACKGROUND OF THE INVENTION

Nuclear magnetic resonance (NMR) techniques are finding increasing use in medical diagnostics. NMR imaging, or magnetic resonance imaging (MRI) as it is sometimes known, has been found to be useful in the detection of a variety of diseases and disorders. MRI has several advantages over other imaging techniques. For example, unlike computerized tomographic methods, MRI does not employ ionizing radiation, and therefore is believed to be safer. Also, MRI can provide more information about soft tissue than can some other imaging methods.

The majority of the NMR techniques developed so far have been based on imaging of hydrogen nuclei. However, other nuclei offer potential advantages with respect to NMR. $^{19}$F in particular is of interest. The fluorine nucleus offers a strong NMR signal magnitude (high gyromagnetic ratio) similar to that of protons. Virtually no imagable fluorine exists naturally in the human body, so no background signal exists; any detectable signal comes only from whatever $^{19}$F has been administered to the subject.

$^{19}$F is a stable isotope and is naturally abundant, so there is no need for isotopic enrichment. Because its gyromagnetic ratio is about 94% that of hydrogen, existing equipment designed to image protons can be inexpensively adapted for $^{19}$F.

As a separate matter, the concept of targeting tissues using antibodies that have been radiolabeled was described years ago (Pressman, D. J. Immunol. 1949, vol. 63, pp 375-388). The advent of hybridoma technology (Kohler, G. and Milstein, C., Nature 1975, vol. 144, pp 873-881) enabled the production of monoclonal antibodies that are homogeneous, each reacting with a single epitope on an antigenic moiety.

Since then a number of monoclonal antibodies have been developed and characterized for their ability to recognize surface antigenic markers that are expressed in high levels on tumor cells and at significantly lower levels (100 to 1,000 fold less) on their normal counterparts. Several such antibodies and their fragments have been used as radiolabeled agents in cancer patients and X-ray images have been obtained (for a summary, see Biotechnology 1992, vol. 10, pp 246). Many other monoclonal antibodies and their fragments have been used in preclinical studies to obtain X-ray images of human tumor grafts in mice and cancerous or other lesions in patients.

Certain of these monoclonal antibodies target well-characterized cancer antigens such as the carcinoembryonic antigen (CEA), the TAG-72 antigen, high molecular weight milk fat globule mucin antigen (HMFG) and the like. Yet others are characterized with respect to their reactivity patterns for different tumor tissues although the molecular characterization of the reactive antigens is not complete (for example, the NR-Lu 10 antibody described by Paul Abrams and colleagues of NeoRx Corporation, B38.1 antibody described by David Colcher and his collaborators and various other antibodies described in the literature).

The use of tools of molecular biology has provided genetically engineered antibodies and their fragments which are either chimeric or humanized wherein the complementary determining regions of, e.g., a mouse monoclonal antibody is grafted into a human antibody molecule (described by Winter and his colleagues from the MRC, England). Yet additional technologies describe the use of combinatorial libraries that express antigen binding fragments encoded by human genetic sequences (described by Richard Lorner and his colleagues).

Although $^{19}$F NMR has potential benefits, there is a need for new and improved $^{19}$F-containing agents, such as $^{19}$F-labeled antibodies, which can be used in NMR imaging and spectroscopy techniques.

SUMMARY OF THE INVENTION

The present invention relates to a $^{19}$F labelled NMR composition which comprises a $^{19}$F-containing sensor moiety and an antibody (or antibody fragment) which reacts specifically with a particular antigen, and which is bound to the $^{19}$F-containing sensor moiety. The amount of $^{19}$F contained by the composition is effective to provide a detectable NMR signal.

In preferred embodiments of the invention, the antibody is a monoclonal antibody, and is specific for a human tumor antigen. The $^{19}$F-containing moiety is preferably selected from the group consisting of fluorinated alkyls, fluorinated acetates, fluoroaniline, and fluoroalkyl phosphonates.

In another embodiment the composition further comprises a spacer moiety, with the $^{19}$F-containing sensor moiety and antibody being bound to the spacer moiety (as opposed to the $^{19}$F-containing sensor moiety being directly bonded to the antibody). The spacer moiety can be used to isolate the $^{19}$F atoms from the substrate, thereby enhancing the NMR signal produced. The spacer moiety can be, for example, an alkyl hydrocarbon having a chain length of approximately 1-100 carbon atoms and containing an amino group. Alternatively, the spacer moiety can be selected from the group consisting of alkyl, alkoxy, aryl, and alkaryl hydrocarbons which contain an amino group, hydrazine, hydrazide, semicarbazide, and hydroxylamine. The spacer moiety can optionally include one or more $^{19}$F atoms.

The present invention also relates to a method of using the above composition, specifically a method of $^{19}$F NMR imaging or spectroscopy (MRI or MRS). The method comprises the steps of: (a) administering to a living mammalian subject, in an amount effective to provide a detectable $^{19}$F NMR signal, a $^{19}$F labelled NMR composition as described above; and (b) detecting the $^{19}$F NMR signal produced thereby by means of $^{19}$F NMR. The signal detected by this method can be used, for example, in tumor imaging.

In one aspect, the present invention relates to the attachment of $^{19}$fluorine to antibodies by direct derivatization or by the linking of $^{19}$fluorinated molecular amplifiers as described elsewhere in this application. The resulting $^{19}$fluorinated antibodies are formulated in a pharmaceutically-acceptable, injectable excipient and used in targeted imaging of lesions such as a tumor mass that displays the antigens reactive with the monoclonal antibody. In a typical situation, the hybridoma cell line or a genetically engineered host cell producing the antibody or its antigen binding domain is cultured in a suitable nutrient medium. The antibody or its antigen binding domain is purified from the harvest by using chromatographic, ultrafiltration and other approaches commonly used by one skilled in the art. The purified antibody or an antigen binding fragment (produced either by cleavage of the antibody enzymatically, chemically or otherwise, or directly from a genetically engineered host) is coupled with $^{19}$fluorine using methods described elsewhere in this application. The $^{19}$fluorinated antibody is separated from unreacted $^{19}$fluorine materials by the use of conventional size separation approaches, tested for specific reactivity to the antigenic target and is then ready for injection in a pharmaceutically acceptable dosage ranging from between about 5 mg to about 50 mg per patient.

Because the $^{19}$F nucleus is very sensitive to changes in its steric and electronic environment, the composition can be used to sense different tissue parameters and cell properties through $^{19}$F NMR spectroscopy, as well as being used for $^{19}$F MRI.

Fluorinated compositions in accordance with the present invention have both diagnostic and prognostic uses, and can serve as physiological probes and cell-function reporters. They can be used not only to delineate tissues at risk and to characterize disease states, but also for monitoring the results of therapy. Specific uses for such compounds include vascular imaging, tumor imaging, and detection of lesions in atherosclerosis, bone metastases, and myocardial infarction. Among the physiologically important parameters that could be sensed are oxygen content, temperature, pH, and the concentration of ions such as Na+, $Ca^{2+}$, and $Mg^{2+}$.

DETAILED DESCRIPTION OF SPECIFIC EMBODIMENTS

A wide variety of antibodies can be used in the present invention. The following table is a list of some suitable monoclonal antibodies, their tumor or antigen target and source:

| Designation | Target | Source |
| --- | --- | --- |
| B72.3; CC49 | Ovary, Colon (TAG-72) | Schlom, J. et al.; NCI, USA |
| SM-3; HMFG 1 | Breast (mucins, milk fat globule) | Taylor, J. et al.; ICRF, UK |
| OVB-3 | Ovary | Pastan, I. et al.; NCI, USA |
| B38.1 | Lung, Colon, Breast, Prostate | Colcher, D. et al.; NCI, USA |
| ING-1 (chimeric) | same as B38.1 | Robinson, R. et al.; XOMA Corp., USA |
| NR-Lu10 | Lung, Colon | Abrams, P. et al.; NeoRx Corp., USA |
| PR-1-A3; UJ 13A | Lung | Bodmar, W. et al.; ICRF, UK |
| 7E11-C5 | Prostate | Gilman, S. et al.; Cytogen Corp., USA |
| Mab 170 | Lung, Colon, Breast, Cervix (adenocarcinomas) | Suresh, M. et al.; Biomira, Inc., Canada |
| Mab 174 | Lung, Head/Neck, Cervix (squamous carcinomas) | Suresh, M. et al.; Biomira, Inc., Canada |
| Mab, B80 | Prostate | Suresh, M. et al.; Biomira Inc., Canada |
| Mab B43 | Ovary | Suresh, M. et al.; Biomira, Inc., Canada |
| 791T36 | Colon | Baldwin, R. et al.; Xoma Corp., USA |
| XMME-1 | Melanoma | Scannon, P. et al.; Xoma Corp., USA |
| R24 | Melanoma | Old, L. et al.; Memorial Sloan Kettering, USA |

Among the suitable $^{19}$F-containing sensor moieties are simple fluorinated alkyls such as $CH_2F$, $CHF_2$, $CF_3$, fluorinated acetates such as $COCH_2F$, $COCHF_2$, and $COCF_3$, as well as fluoroaniline (useful for sensing pH), fluorinated pyrophosphate analogs such as fluoroalkyl phosphonates, fluorinated polyamines, fluorinated porphyryns and their metal complexes, fluorinated histochemicals, and fluorinated biotin or avidin.

Methods of fluorination in accordance with the present invention can suitably be by one of the following methods.

The hydroxyl groups of a polymer can be replaced by $^{19}$F atoms, using chemical, enzymatic, or a combination of chemical and enzymatic methods. Partial hydroxyl replacement can be accomplished by using diethylaminosulfur trifluoride (DAST) as a fluorinating agent.

Alternatively, CHO groups on the polymer can be replaced by $^{19}$F using DAST.

As another option polymeric hydroxyl groups can be esterified, for example:

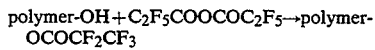

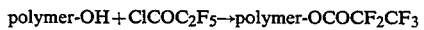

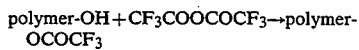

Also, hydroxyl groups could be oxidized using reagents such as periodate, and then coupled to the amino groups of $^{19}$F-labelled compounds, then reduced with reagents such as $NaBH_4$.

Polymer hydroxyl groups could be activated by cyanogen bromide and then coupled to a fluorinated amine, yielding an iminocarbonic acid ester.

Polymer hydroxyl groups, such as in a dextran polymer, can be utilized to form 3-bromo-2-hydroxyl propyl dextrans, which can be transformed into epoxide derivatives. The epoxide derivative is highly reactive and in alkaline solution at room temperature can be coupled with substances containing nucleophilic groups like alkyl and aryl primary amines, hydroxyl groups, and thiol groups. For example:

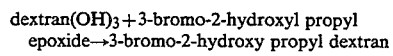

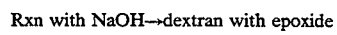

A=O, S, NH
R=organic fluorine-containing moiety

Fluorinated amines can be attached to polysaccharides. For instance, carboxymethyl-cellulose can be esterified to produce the methyl ester which, on treatment with hydrazine hydrate, forms hydrazide. The hydrazide on diazotization with Hcl and $NaNO_2$ forms a reactive azide. The azide in alkaline solution will react rapidly with amines to form the covalently bonded product polymer-CONHR, where R is a fluorinated aliphatic or aromatic amine.

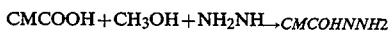
CMCOOH + CH₃OH + NH₂NH → CMCOHNNH₂

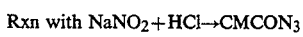
Rxn with NaNO₂ + HCl → CMCON₃

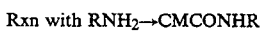
Rxn with RNH₂ → CMCONHR

Aminodextrans can be fluorinated using S-ethyl thiol trifluoroacetate (SETFA) as a fluorinating agent. Acylation of available amino groups can be accomplished by using an excess of SETFA as the acylating reagent.

Alternatively, amino groups can be acylated using acid fluorides (anhydrides).

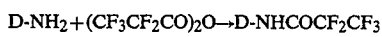
D-NH₂ + (CF₃CF₂CO)₂O → D-NHCOCF₂CF₃

D-NH₂ + ClCO-AR → D-NHCO-AR

AR = aromatic ring containing F

D-NH₂ + ClCO-AR-LF₃ → D-NHCO-AR-LF₃

AR = aromatic ring
L = alkyl chain

Other possible reactions include acylation using fluorinated propionic anhydride, succinic anhydride (for example—trifluoroacetamido succinic anhydride) reactions with fluorinated phenyl isothiocyanate, and reactions with fluorinated alkyl isothiocyanate.

Where antibodies or fragments thereof are used, the sensor moieties can be selectively attached to sites not directly involved in antibody-antigen binding, thereby allowing the antibody to retain its immunoreactivity. Possible sites for attachment include carbohydrate groups, amino groups, sulfhydryl groups, or combinations thereof.

The following specific examples illustrate the preparation of compounds in accordance with the present invention.

N-Trifluoroacetamide D-Glucose

Glucosamine in anhydrous methanol was treated with s-ethyl thiol trifluoroacetate (SETFA) as described by Wolform and Conigliaro, *Carbohydrate Research*, 11, 63 (1969). A suspension of 2-amino-deoxy-D-glucose hydrochloride (10 g) in 50 ml anhydrous methanol was treated with an equivalent amount of sodium methoxide in methanol (1.06 g of Na in 10 ml methanol). The mixture was stirred (magnetic stirrer) till a clear solution was obtained. NaCl precipitate remained at the bottom. To this, SETFA (10 g) was added. The reaction mixture was stirred at room temperature for 24 hrs. The solution was evaporated to a solid residue and the residue was extracted with hot acetone. Ether was added to the cooled acetone extract and the mixture was refrigerated overnight. The white crystalline compound was recrystallized from a mixture of acetone-ether to obtain shiny crystals.

Results
Yield: 8.2 g. MP: 193–195° C.

Analysis

| | Element: | | | |
|---|---|---|---|---|
| | C | H | N | F |
| Calculated: | 34.92 | 4.40 | 5.09 | 20.72 |
| Found: | 36.89 | 4.75 | 4.92 | 20.75 |

The product was soluble in water. Elemental analysis data were in agreement with the calculated values.

Proton and F-19 NMR data confirmed the formation of N-trifluoroacetamido-D-glucose.

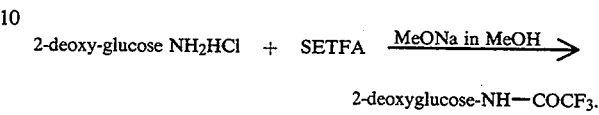
2-deoxy-glucose NH₂HCl + SETFA $\xrightarrow{\text{MeONa in MeOH}}$ 2-deoxyglucose-NH—COCF₃.

Trifluoroacetyl-DL-Lysine

Trifluoroacetyl-DL-lysine was obtained by treating DL-lysine monohydrochloride with s-ethyl thiol trifluoro acetate (SETFA) in basic solution, as described in Schallenberg and Calvin, JACS 77, 2779 (1955).

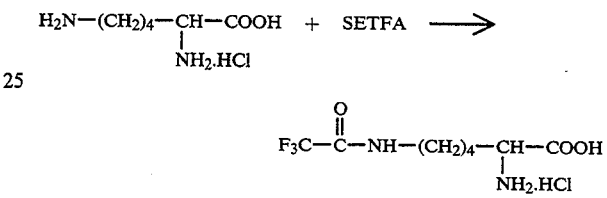
$$H_2N-(CH_2)_4-\underset{\underset{NH_2 \cdot HCl}{|}}{CH}-COOH + SETFA \longrightarrow$$

$$F_3C-\underset{\underset{}{\overset{O}{\|}}}{C}-NH-(CH_2)_4-\underset{\underset{NH_2 \cdot HCl}{|}}{CH}-COOH$$

SETFA (4.0 ml) was added to DL-lysine monohydrochloride 3.6 g (20 mmol), dissolved in 20 ml of 1N NaOH. The heterogeneous mixture was stirred for 6 hours at room temperature and cooled for 1 hour in an ice cold water bath.

The solid that separated was filtered and washed with cold water. It was recrystallized from ethanol.

Results

Yield: 0.8 g (16%) (Loss of product due to washing with cold water).

MP: 262°–263° C.

H-1 NMR: 3.82 δ CH; J=1.5, 1.7, 1.96, 3.41 (Solvent D₂O).

F-19 NMR: Sharp signal (solvent D₂O).

| | Elemental Analysis: | | | |
|---|---|---|---|---|
| | C | H | N | F |
| Found: | 39.87 | 5.45 | 11.61 | 23.52 |
| Calculated: | 39.67 | 5.41 | 11.57 | 23.55 |

Aminodextrans

Aminodextrans (molecular weight: 10k, 40k, and 70k) were obtained from Molecular Probes, Inc., Portland, Oreg.

| Molecular Size | Number of amino groups per molecule |
|---|---|
| 10k | 6.8 |
| 40k | 13 |
| 70k | 30 |

Aminodextran molecule was reacted with s-ethyl thioltrifluoroacetate (SETFA) in a formamide and pyridine mixture to yield a product in which the amino groups of the aminodextrans were modified with trifluoracetyl moiety, as described in Goldberg and Anfinsen, Biochem., 1, 401 (1962).

The general synthesis procedure was as follows: Aminodextran was dissolved in formamide and pyridine (2:1 v/v). S-ethylthioltrifluoroacetate (SETFA) was added slowly with stirring. The mixture was stirred overnight. The desired product was precipitated with cold ethanol and further purified by dialysis against water, and the powdered product obtained by lyophilization.

As a specific example, aminodextran 70k (0.6 g) was dissolved in 10 ml formamide by stirring for 2-3 hours. Pyridine 5 ml was added, and stirring continued until the homogeneous solution was obtained. The pH was approximately 7 by paper. S-ethylthioltrifluoroacetate 3 ml was added dropwise for a period of 30 minutes with vigorous stirring. This reagent is immiscible with the above solvent system. However, it forms small droplets and slowly undergoes reaction which could be seen by the fall in pH values and homogeneity of the solution. The mixture was stirred overnight and poured on chilled ($-12°$ C.) absolute ethanol (150 ml) with vigorous stirring. The white precipitate obtained was held at $-12°$ C. for an additional 4 hours with stirring. The precipitated product was centrifuged and washed with ethyl alcohol. The product was dissolved in distilled water and dialyzed against distilled water for 24 hours with 6 changes using 1000 ml of water each time. The dialyzed solution was centrifuged and the clear solution was lyophilized to obtain a white silky solid.

Yield: 0.56 g
TLC Matrix: silica gel 60A, MK6F, Whatman
Solvent: Pyridine/acetic/acid water (9:1:90, v/v/v)
Detection: 50% $H_2SO_4$
$R_f$ of starting material: 0.41
$R_f$ of final product: 0.74
Proton NMR spectra: Typical polymeric appearance
F-19 NMR spectra: Single (Fluorine) sharp signal

| | Elemental Analysis | | | |
|---|---|---|---|---|
| | C | H | N | F |
| Calculated*: | 43.87 | 5.94 | 1.11 | 2.88 |
| Found: | 40.65 | 5.78 | 0.62 | 2.26 |

*percentages of elements calculated by assuming the molecular weight of dextran to be 70k.

Results

Trifluoroacetylated aminodextran 10K and 40K:
10K: TLC analysis:
Solvent system: pyridine/acetic acid/$H_2O$ (9:1:90)
$R_f$ of starting material: 0.5
$R_f$ of final product: 0.84
NMR spectra analysis:
Proton spectra: Typical polymeric compounds ($D_2O$)
F-19 spectra: Single fluorine, sharp signal ($D_2O$)

| | Elemental analysis: | | | |
|---|---|---|---|---|
| | C | H | N | F |
| Found: | 40.01 | 5.65 | 0.83 | 2.50 |

| | -continued | | | |
|---|---|---|---|---|
| | Elemental analysis: | | | |
| | C | H | N | F |
| Calculated*: | 43.56 | 5.81 | 1.39 | 4.13 |

*percentages of elements calculated by assuming the molecular weight of dextran to be 10K.

40K: TLC analysis:
Solvent system: pyridine/acetic acid/$H_2O$ (9:1:90)
$R_f$ of starting material: 0.48
$R_f$ of final product: 0.76
NMR spectra analysis:
Proton spectra: Typical polymeric ($D_2O$)
F-19 spectra: Single fluorine, sharp signal

| | Elemental analysis: | | | |
|---|---|---|---|---|
| | C | H | N | F |
| Found: | 40.82 | 5.97 | 0.61 | 1.58 |
| Calculated*: | 43.92 | 5.98 | 0.99 | 2.35 |

*percentages of elements by assuming the molecular weight of dextran to be 40K.

Trifluoroacetylation of Poly-L-Lysine

General Procedure:

Trifluoroacetylation of poly-L-lysine is carried out with S-ethyl thioltrifluoroacetate in dimethylformamide, as described in Levy and Paselk, Biochem. Biophys. Acta, 310, 398-405 (1973). The amino groups of poly-L-lysine are modified with the trifluoroacetyl moiety.

Poly-L-lysine.HBr (molecular weight 8,800) was reacted with S-ethyl-thioltrifluoroacetate in dimethylformamide. Poly-L-lysine.HBr (100 mg, 11.36 μmoles) was dissolved in 20 ml of DMF with stirring, for 30 minutes when an almost clear solution was obtained. Triethylamine (TEA) 50 μl was added (appearance of precipitate noted) and the stirring continued for 15 minutes. S-ethylthioltrifluoroacetate (SETFA 51.737 mg, 327.17 μmoles), dissolved in 1 ml of DMF, was added dropwise to the reaction mixture with constant stirring for 15 minutes. The pH was adjusted after each addition of SETFA. A clear solution obtained at the end, was stirred for another 90 minutes and then poured onto chilled absolute ether. The solution was decanted. The precipitate was centrifuged and then dissolved in 15-20 ml water and dialyzed against distilled water at 41° C. for 48 hours. The shiny powdery product was obtained by lyophilization of the dialyzed solution.

Results

Yield: 20 mgs
F-19 NMR spectra: A sharp single fluorine signal ($D_2O$)
Trifluoroacetamido-succinylated Poly-L-Lysine:
Poly-L-Lysine (50 mg, 5.68 μMol) in 20 ml phosphate buffer (pH=7.24) was reacted with (120 mg) trifluoroacetamidosuccinic anhydride for 30 minutes. General procedure for preparation of succinylated Poly-L-Lysine is described by W. B. Stason, M. Vallotton and E. Haber; Biochem. Biophys. Acta. 133:582-584 (1967). The product was purified by exhaustive dialysis against d. water and lyophilized to obtain white solid.

One way of producing a stronger signal from trifluoroacetylated aminodextrans would be to trifluoroacetylate the hydroxyl groups instead of the amino groups, which will dramatically increase the number of available sites, and therefore increase the concentration of $^{19}F$ in the molecule. The in vivo NMR signal can also be optimized by using spacer moieties to separate the $^{19}F$ from the substrate.

In the NMR methods of the present invention, the $^{19}F$-labelled compound is administered to a living subject, preferably parenterally or orally. They can suitably be administered in a formulation containing one or more of the $^{19}F$-labelled compounds and a pharmaceutically acceptable diluent or carrier.

The preceding description is intended to illustrate specific embodiments of the present invention, not to provide an exhaustive description of all possible embodiments of the invention. Persons skilled in this field will recognize that modifications could be made to the preceding examples which would still be within the scope of the present invention.

We claim:

1. A $^{19}F$ labelled NMR composition, comprising:
   a $^{19}F$-containing sensor moiety, where the sensor moiety comprises —$COCF_3$ or —$NHCOCF_3$, and the sensor moiety produces a single $^{19}F$ NMR signal; and
   an antibody or antibody fragment which reacts specifically with a particular antigen, and which is bound to the $^{19}F$-containing sensor moiety;
   where the amount of $^{19}F$ contained by the composition is effective to provide a detectable NMR signal.

2. The composition of claim 1, where the antibody is a monoclonal antibody.

3. The composition of claim 1, where the antibody is specific for a human tumor antigen.

4. The composition of claim 1, further comprising a spacer moiety, with the $^{19}F$-containing sensor moiety and antibody being bound to the spacer moiety.

5. The composition of claim 4, where the spacer moiety is an alkyl hydrocarbon having a chain length of approximately 1–100 carbon atoms and containing an amino group.

6. The composition of claim 4, where the spacer moiety is selected from the group consisting of alkyl, alkoxy, aryl, and alkaryl hydrocarbons which contain an amino group, hydrazine, hydrazide, semicarbazide, and hydroxylamine.

7. A method of NMR imaging or spectroscopy, comprising the steps of:
   (a) administering to a living mammalian subject, in an amount effective to provide a detectable $^{19}F$ NMR signal, a $^{19}F$ labelled NMR composition which comprises:
   a $^{19}F$-containing sensor moiety, where the sensor moiety comprises —$COCF_3$ or —$NHCOCF_3$, and the sensor moiety produces a single $^{19}F$ NMR signal; and
   an antibody or antibody fragment which reacts specifically with a particular antigen, and which is bound to the $^{19}F$-containing sensor moiety;
   where the amount of $^{19}F$ contained by the composition is effective to provide a detectable NMR signal; and
   (b) detecting the $^{19}F$ NMR signal produced thereby by means of $^{19}F$ NMR.

8. The method of claim 7, where the detected $^{19}F$ NMR signal is used for tumor imaging.

9. The method of claim 7, where the antibody is a monoclonal antibody.

10. The method of claim 7, where the antibody is specific for a human tumor antigen.

11. The method of claim 7, where the composition further comprises a spacer moiety, with the $^{19}F$-containing sensor moiety and antibody being bound to the spacer moiety.

12. The method of claim 11, where the spacer moiety is an alkyl hydrocarbon having a chain length of approximately 1–100 carbon atoms and containing an amino group.

13. The method of claim 11, where the spacer moiety is selected from the group consisting of alkyl, alkoxy, aryl, and alkaryl hydrocarbons which contain an amino group, hydrazine, hydrazide, semicarbazide, and hydroxylamine.

14. The method of claim 7, where the $^{19}F$-containing sensor moiety is a trifluoroacetamidosuccinate group.

15. The composition of claim 1, where the $^{19}F$-containing sensor moiety is a trifluoroacetamidosuccinate group.

* * * * *

UNITED STATES PATENT AND TRADEMARK OFFICE
CERTIFICATE OF CORRECTION

PATENT NO. : 5,422,094
DATED : Jun. 6, 1995
INVENTOR(S) : Peter P. Antich, et al It is certified that error appears in the above-indentified patent and that said Letters Patent is hereby corrected as shown below:

Column 5, line 5, "$CMCOOH + CH_3OH + NH_2NH \rightarrow CMCOHNNH2$" should be

--$CMCOOH + CH_3OH + NH_2NH_2 \rightarrow CMCOHNNH_2$--.

Signed and Sealed this

Tenth Day of October, 1995

*Attest:*

BRUCE LEHMAN

*Attesting Officer*  *Commissioner of Patents and Trademarks*